United States Patent [19]

Joly et al.

[11] Patent Number: 5,712,213
[45] Date of Patent: Jan. 27, 1998

[54] REJUVENATION PROCESS FOR A SOLID ALKYLATION CATALYST

[75] Inventors: Jean-François Joly, Lyons; Eric Benazzi, Montesson; Christian Marcilly, Houilles; Jean-Paul Euzen, Dardilly; Alain Forestiere, Vernaison, all of France

[73] Assignee: Institut Francaise Du Petrole, Rueil-Malmaison, France

[21] Appl. No.: 493,462

[22] Filed: Jun. 22, 1995

[30] Foreign Application Priority Data

Jun. 22, 1994 [FR] France .................................. 94 07855

[51] Int. Cl.⁶ ........................... B01J 20/34; B01J 38/56
[52] U.S. Cl. ........................................... 502/31; 502/29
[58] Field of Search ...................... 502/31, 29; 585/721

[56] References Cited

U.S. PATENT DOCUMENTS

| | | | |
|---|---|---|---|
| 3,729,526 | 4/1973 | Anderson | 260/683.48 |
| 3,852,371 | 12/1974 | Kemp | 260/683.47 |
| 3,855,343 | 12/1974 | Huang et al. | 260/683.44 |
| 3,879,489 | 4/1975 | Yurchak et al. | 260/683.44 |
| 4,071,576 | 1/1978 | Behrmann et al. | 260/683.47 |
| 5,444,175 | 8/1995 | Joly et al. | 585/714 |
| 5,491,278 | 2/1996 | Angstadt et al. | 585/731 |

FOREIGN PATENT DOCUMENTS 0 584 006  2/1994  European Pat. Off. .......... C07C 2/58

*Primary Examiner*—Glenn A. Caldarola
*Assistant Examiner*—Alexander G. Ghyka
*Attorney, Agent, or Firm*—Millen, White, Zelano & Branigan, P.C.

[57] ABSTRACT

The invention concerns a rejuvenation process for a solid catalyst for the alkylation of at least one isoparaffin by at least one olefin. The process is characterised in that the catalyst is rejuvenated in the reaction zone by circulating an isoparaffin-rich liquid fraction over the bed, said fraction originating from a zone for separating the reaction effluent extracted from the reaction zone.

20 Claims, 1 Drawing Sheet

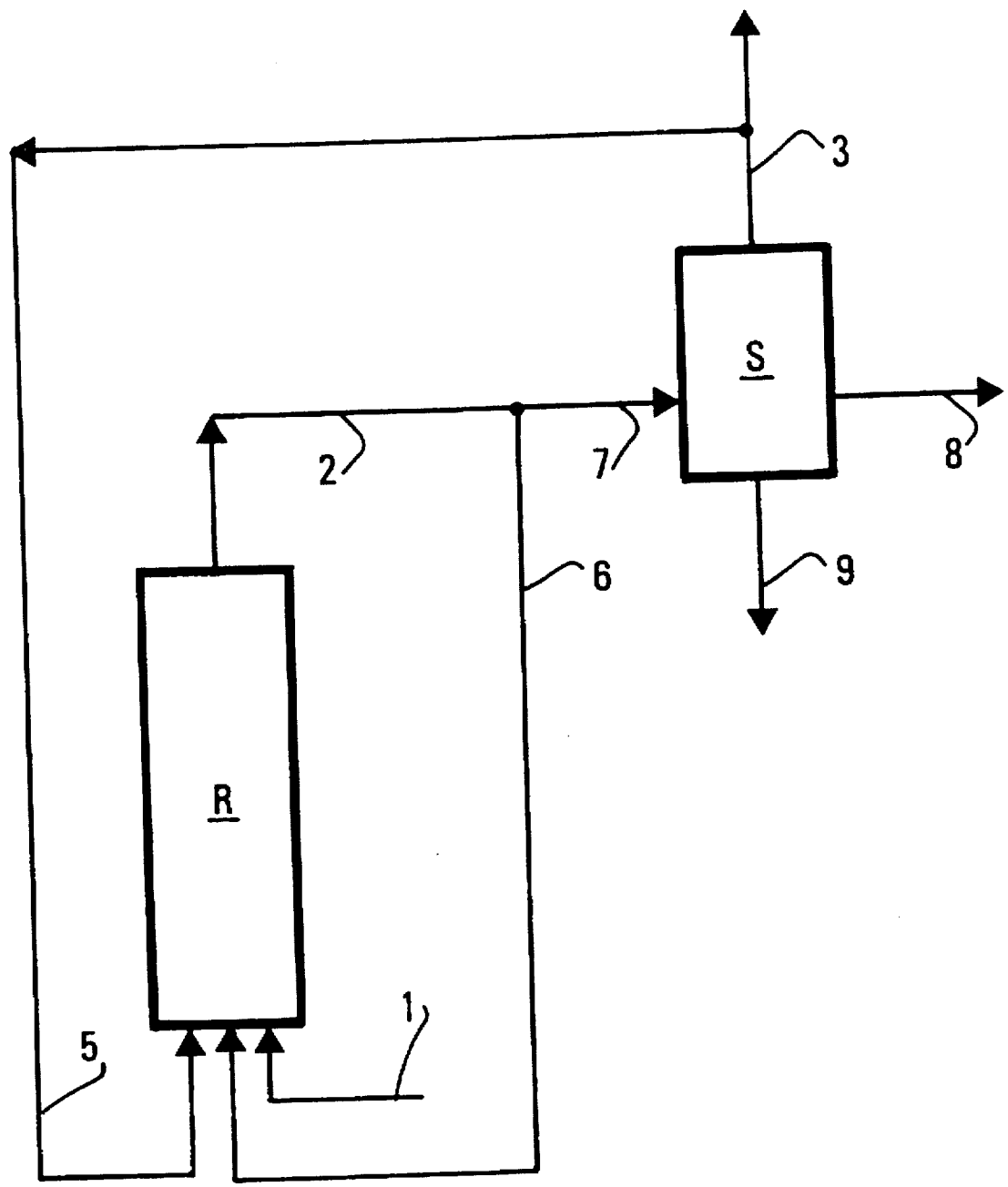

REJUVENATION PROCESS FOR A SOLID ALKYLATION CATALYST

BACKGROUND OF THE INVENTION

The present invention concerns a novel process for the alkylation of at least one isoparaffin, preferably isobutane, by at least one olefin containing 3 to 6 +1carbon atoms per molecule.

It is particularly important for spark ignition internal combustion engines, in particular those with high compression ratios, to use fuels with high octane numbers, i.e., essentially constituted by highly branched paraffin hydrocarbons. Alkylation of isoparaffins (isobutane and/or isopentane) by olefins containing 3 to 6 carbon atoms per molecule can produce such products. This reaction requires the use of highly acidic catalysts, primarily to reduce side reactions such as hydride abstraction from the olefin and polymerisation, which produces less branched hydrocarbons with low octane numbers and unsaturated hydrocarbons, also cracking reactions and dismutation reactions.

Existing processes for the production of hydrocarbons by alkylation of isobutane with olefins generally use either sulphuric acid or hydrofluoric acid as a catalyst. In these processes, the acidic catalyst constitutes a liquid phase which is brought into contact with the liquid isobutane-olefin mixture to form an emulsion. These processes are costly and pose substantial problems as regards personnel and environmental safety. In order to overcome these problems, catalytic systems other than those using liquid phase sulphuric acid and hydrofluoric acid have been sought.

The present invention concerns a catalytic process for the alkylation of isoparaffins (in particular isobutane and/or isopentane) by an olefin, to produce at least one product, for example from the group constituted by dimethylbutanes, trimethylpentanes, trimethylhexanes and trimethylheptanes, in which the olefin and/or a mixture of olefins is introduced into the reaction zone in the liquid phase and mixed with the isoparaffin and/or a mixture of isoparaffins.

The process of the invention enables alkylation of isobutane by olefins to be carried out under improved conditions. The reaction is characterised by high exothermicity (about 20 kcal/mole of olefin (in particular butene) transformed). In particular, the process produces good homogeneity of temperature and reactant concentration.

The operating conditions in the alkylation process for at least one isoparaffin of the present invention, in particular the temperature and pressure, are selected so that the mixture constituted by the isobutane, the olefins and the reaction products, is liquid. In addition, it is important that the catalyst is immersed in this liquid to ensure good overall liquid-solid contact. This avoids the appearance of dry zones in the reactor, these zones being probably responsible for lack of thermal stability, since the dry zones can reach high temperatures due to the fact that the reaction can occur in these areas entirely in the gas phase. A number of techniques have been proposed which use a continuous liquid phase, the catalyst being used in the form of a suspension, an ebullated bed or as a mobile or fixed bed.

Examples of solid acid catalysts used in such processes are: molecular sieves, macroreticular resins which may be combined with boron trifluoride ($BF_3$), perfluorinated resins, Lewis acids and/or Brönsted acids deposited on a variety of inorganic supports, chlorinated aluminas, graphites with intercalated Lewis and/or Brönsted acids, and anions deposited on oxide supports such as $ZrO_2/SO_4$. These processes can be divided into two types: (i) the catalyst is placed in suspension in a hydrocarbon phase by vigorous agitation in the reactor, as in a perfectly agitated reactor; (ii) the catalyst is in a fixed bed in the reactor.

Processes of type (i) include those described in United States patents U.S. Pat. No. 3,879,489 and U.S. Pat. No. 3,855,343; this type of operation has a major drawback: the catalyst can be rapidly destroyed by attrition which introduces the problem of eliminating the fine particles. An improvement to the operation of a process of type (ii) is described in U.S. Pat. No. 3,852,371 which proposes injecting the isoparaffin(s) olefin(s) feed into the catalyst bed at different levels, with partial recycling to the same levels, which would appear to be more difficult to achieve. U.S. Pat. No. 3,852,371 and U.S. Pat. No. 5,073,665, which refer to a preferred fixed bed operation, describe the partial recycling of the effluent leaving the reactor to the reactor inlet. U.S. Pat. No. 5,073,665 describes an embodiment comprising at least one fixed catalyst bed with one olefin supply for each fixed catalyst bed.

U.S. Pat. No. 5,157,196 claims the use of alkylation catalysts in a circulating bed, characterised in that a catalyst washing zone which is different to the reaction zone is present which functions as a fluid bed. The residence time for the hydrocarbons in the reactor is short (1 second to 5 minutes).

The present invention concerns a novel process for the alkylation of isoparaffins (isobutane and/or isopentane) in the presence of a heterogeneous catalyst, and is characterised in that the catalyst is in a reaction zone R in suspension in a hydrocarbon phase in the liquid state. Zone R can operate as a fixed bed, expanded bed, mobile bed or as a perfectly agitated reactor (Grignard), ebullated bed, fluid bed or any other equivalent form.

More precisely, the invention concerns a process for the rejuvenation of a solid catalyst for the alkylation of at least one isoparaffin by at least one olefin containing 3 to 6 carbon atoms per molecule, characterised in that said rejuvenation is carried out at least periodically in the reaction zone by circulating at least a fraction which is rich in the isobutane obtained after fractionation or separation of the reaction effluent over the catalytic bed (i.e., by washing the catalyst). The means used in the present invention for washing the catalyst (whether in the reaction zone in the form of an expanded bed, ebullated bed, fluid bed, agitated bed or any other equivalent form) are thus essentially the recycling of specifically selected fractions of reaction effluent. The recycle(s) in question are effected at least partially to the inlet to the reaction zone (i.e., generally to the lower portion of the reaction zone), but also, and preferably, to other levels in the reaction zone so that the whole of the catalytic bed is in contact with the recycle effluents.

BRIEF DESCRIPTION OF THE INVENTION

The process of the invention is also characterised in that a treatment termed rejuvenation is periodically carried out, the treatment comprising, by way of example, at least the following four steps which are illustrated in the single FIGURE which is schematic flowsheet:

DETAILED DESCRIPTION OF THE FIGURE step 1: the supply of a feed (i) introduced by line 1 to a reaction zone R containing a catalytic bed (the feed is a mixture of olefins and isoparaffin) is stopped.

step 2: the catalyst is generally separated from the liquid hydrocarbon phase present in reaction zone R. The liquid phase is then extracted, (i.e., withdrawn) via line 2 from reaction zone R and sent to a separation zone S. The catalyst remains in reaction zone R during the extraction.

step 3: an isoparaffin-rich liquid phase (line 3) from the head of separation zone S (compound (iii)) is introduced at least in part into reaction zone R via line 5. The catalyst can at this stage be brought into suspension in the liquid phase.

This rinsing operation can be repeated a number of times and the washing effluent can be returned to the normal separation zone S each time.

Steps 2 and 3 can be carried out in a single step: when rejuvenation is carried out, the reactor concerned is directly connected to separation section S and is only supplied, via lines 3 and 5, by the light effluent from section S (mainly isoparaffin).

Washing can, of course, be carried out in co-current or counter-current mode when the catalyst is arranged as an expanded bed.

step 4: the temperature and pressure conditions are brought to alkylation reaction values, the feed (i) described in step 1 above is introduced into reaction zone R and thus comes into contact, for example, with a catalyst which is bathed in the isoparaffin if using a fixed bed, or with a suspension of the catalyst in the isoparaffin if using an expanded or an agitated Grignard type bed.

Steps 2 and 3 can be repeated a number of times.

The inventive catalyst rejuvenation treatment described by the succession of steps described above is periodically repeated. This treatment is not a regeneration of the catalyst but a treatment which conserves enough of the activity of the catalyst so that regeneration of the catalyst is only necessary after a lengthy period. The alkylation catalyst is thus subjected to reaction-rejuvenation cycles. One of the advantages of the process of the present invention is that the catalyst remains permanently in the reaction zone R during the reaction-rejuvenation cycles.

The process of the present invention is suitable for any heterogeneous catalyst for carrying out the alkylation of isoparaffin, in particular isobutane and/or isopentane, by olefins containing 3 to 6 carbon atoms per molecule.

The catalyst present in zone R is selected from solid catalysts which are known to the skilled person. Preferably, the catalyst is selected from the following catalysts:

a catalyst containing at least sulphuric acid impregnated into a porous organic or inorganic support, such as the catalysts described in French patent applications FR-A-2 682 891, FR-A-2 683 740, FR-A-2 683 739 and FR-A-2 687 935.

a catalyst comprising a mixture containing at least one halide of a compound selected from the group formed by aluminium and boron and at least one quaternary ammonium halide and/or amine halohydrate, such as the catalyst described in French patent application FR-A-2 686 526.

The catalyst used in the present invention preferably comprises silica and sulphuric acid, the silica being totally impregnated with the sulphuric acid. The silica is characterised in that its pore volume is greater than 0.5 cm$^3$/g. The catalyst obtained after impregnation is characterised in that the sulphuric acid content is greater than 40%, preferably greater than 70% by weight.

The silica can contain impurities such as oxides, alkalis, alkaline-earths, aluminium compounds or any other impurity known to the skilled person, the total quantity of these impurities not exceeding 2% by weight with respect to the silica.

The sulphuric acid concentration is advantageously between 90% and 100% by weight, preferably between 97% and 100% by weight, more preferably between 98% and 100% by weight.

Prior to impregnation, additives aimed at improving catalytic performance can be added to the $H_2SO_4$ acid phase. Examples of additives are trifluoromethane sulphonic acid $CF_3SO_3H$ and the acid $HB(SO_4H)_4$. Preferred catalysts for use in the present invention (of the type sulphuric acid on silica, preferably doped with a boron compound) produce better results that those which would be obtained with more conventional catalysts of the type silica doped with $SbF_3$ or $SbF_5$.

The average diameter of the catalyst particles, mainly constituted by substantially spherical particles, used in the process of the invention is generally between 0.1 and 150 microns (1 micron=$10^{-6}$ m), preferably between 5 and 110 microns, and more preferably between 5 and 80 microns.

The process of the present invention is an alkylation process in which a feed comprising at least one isoparaffin, preferably selected from the group formed by isobutane and isopentane, more preferably isobutane, and at least one olefin containing 3 to 6 carbon atoms per molecule, is treated in the presence of a solid alkylation catalyst; said process comprises:

a) introducing the following compounds or elements into the reaction zone and bringing them into contact with the catalyst present therein:
  (i) the feed, preferably introduced at least at the inlet to zone R, via line 1,
  (ii) optionally, the liquid effluent described at b), introduced at least at the inlet to zone R, preferably entirely introduced at the inlet to zone R, and
  (iii) the liquid effluent described at d), preferably introduced at least at the inlet to zone R, b) optionally recycling a portion of the liquid reaction effluent leaving via line 2 to reaction zone R via line 6 to the inlet to reaction zone R, c) introducing at least a portion of the liquid effluent leaving reaction zone R to a fractionation or separation zone S for the isobutane/normal/paraffin/alkylate via line 7, d) recycling a major portion of the isoparaffin-rich liquid effluent extracted from zone S to reaction zone R via lines 3 and 5, e) obtaining an alkylate as a product, extracted via line 8 from the lower portion of zone S, and f) obtaining normal-paraffin as a purge from zone S via line 9.

The process of the present invention is also characterised in that the catalyst is periodically rejuvenated using the five-step process described above, in which during the rejuvenation step, the supply of feed
  (i) to reaction zone R is stopped.

In accordance with a preferred implementation of the process of the invention, the feed, i.e., the compound (i) described in a), is introduced at several points in zone R.

In accordance with another preferred implementation of the process of the invention, compound (ii) described at a) is introduced at several points in zone R, in particular to different levels of the catalytic bed.

Preferably, the fractions of compounds (i) to (iii) described at a) which are introduced into zone R are mixed together partially or completely, preferably completely, before being introduced into the zone.

The temperature in reaction zone R is generally between −15° C. and +6° C., preferably between −15° C. and 0° C.

Preferably, the feed has been dried over a molecular sieve and selectively hydrogenated before introduction into reaction zone R to eliminate the major part of at least the highly unsaturated compounds which the feed may contain and which can inhibit the catalytic phase.

The reactants are introduced so that the hourly space velocity, expressed as the weight of olefin introduced per unit weight of catalyst present in zone R per hour, is generally between 0.01 and 10 $h^{-1}$, preferably between 0.02 and 2 $h^{-1}$, more preferably between 0.05 and 1 $h^{-1}$.

The concentration per unit volume of the catalyst in reaction zone R, expressed as the volume of catalyst per volume of liquid phase hydrocarbon, is between 1:100 and 1:1, preferably between 1:100 and 1:50, more preferably between 1:50 and 1:4.

In order to limit secondary reactions, an excess of isoparaffin with respect to the olefin is used at the inlet to reaction zone R. By way of example, when alkylating isobutane by a butene, the isobutane can be introduced into the feed either pure or in the form of a mixture of butanes containing, for example, at least 40% of isobutane. In addition, a butene can be introduced either pure or as a mixture of butene isomers. In all cases, the isobutane/butene molar ratio at the inlet to reaction zone R is generally between 5 and 1000, preferably between 5 and 500 and more preferably between 10 and 200.

In order to limit secondary reactions involving degradation of the $C_5$-$C_{12}$ isoparaffins present in the liquid effluents passing through reaction zone(s) R, the separation or fractionation operation is carried out in zone S so that the ratio of the molar flow rates of the isoparaffin (for example isobutane) at the head of separation zone S and the alkylate at the bottom of zone S is between 5:1 and 100:1, preferably between 10:1 and 50:1.

The rejuvenation treatment for the catalyst bed used in the present invention and present in reaction zone R is carried out at a frequency (or cycle) corresponding to the age of the catalyst, expressed as the weight of alkylate produced per weight of catalyst, of between 0.01 and 50 g/g, preferably between 0.1 and 25 g/g and more preferably between 0.1 and 5 g/g. The period corresponding to carrying out the four steps described above is advantageously between 1 minute and 10 hours, preferably between 1 minute and 5 hours.

One or more reactors can be used in the process of the invention. When using several reactors in series, it is advantageous to introduce the isoparaffin of the feed (compound (i)) and from separation zone S (compound (iii)) to the inlet to the first reactor, and to introduce the olefins to the inlet to each of the reactors.

When using the reactors in parallel, each of the reactors receives a portion of the common effluent (recycle) along with appropriate quantities of olefins (for example butenes) (cooled and recycled from the head of distillation column S) using distribution systems which are well known to the skilled person.

When using several reactors, at least one reactor is in the rejuvenation cycle, the others being in the reaction cycle (swing technique).

In a preferred implementation of the process of the present invention, the catalyst in the reactors can be renewed. This is accomplished by extracting at least a portion of the deactivated catalyst, i.e., after several rejuvenation treatments, held in suspension using any means known to the skilled person, and fresh catalyst or ex situ regenerated catalyst is introduced into reaction zone R. The quantity of catalyst extracted equals the amount of catalyst introduced. This replacement operation preferably takes place at the end of a rejuvenation operation.

We claim:

1. A process for the rejuvenation of a solid catalyst for the alkylation of at least one isoparaffin by at least one olefin containing 3 to 6 carbon atoms per molecule, characterized in that said rejuvenation is carried out in the reaction zone, at least periodically, by circulating at least a portion of an isoparaffin-rich fraction obtained by fractionation or separation of the liquid reaction effluent from the reaction zone over the catalytic bed, the process being characterised in that the reaction zone R containing a catalytic bed is supplied with a feed (i) comprising at least said isoparaffin and said olefin introduced at least partially to the base of the reaction zone, and in that:
   the supply of feed is periodically stopped for a sufficient time to enable the catalyst in the reaction zone to be washed,
   the reaction effluent is extracted and the catalytic bed remains substantially in the reaction zone R,
   the reaction effluent is separated or fractionated in a zone S to recover at least an isoparaffin-rich fraction, at least a portion of this fraction being recycled to the reaction zone to wash said catalyst while said feed to the reaction zone is stopped, and,
   the reaction is restarted by restarting the supply of feed (i) to the reaction zone.

2. A process according to claim 1 in which the isoparaffin is selected from the group consisting of isobutane and isopentane.

3. A process according to claim 1, in which the catalytic bed is selected from the group consisting of a fixed, expanded, ebullated or agitated bed.

4. A process according to claim 1, in which extraction of the reaction effluent from the reaction zone and recycling to said reaction zone of an isoparaffin-rich fraction are carried out substantially simultaneously.

5. A process according to claim 4, characterised in that it is repeated periodically.

6. A process according to claim 1 in which feed (i) is introduced at several points in the reaction zone, these points being located at different levels.

7. A process according to claim 4, in which:
   (a) the following compounds or elements are introduced into the reaction zone:
      (i) a feed,
      (ii) optionally, at least a portion of the reaction effluent,
      (iii) an isoparaffin-rich effluent from the reaction effluent,
   (b) after optionally stopping the alkylation reaction, extracting the reaction effluent and optionally recycling a portion of this reaction effluent designated (ii), to step (a) to the reaction zone,
   (c) sending at least a portion of said reaction effluent to a separation or fractionation zone,
   (d) recycling at least a portion of an isoparaffin-rich fraction extracted from said zone S and designated (iii) in step (a), to the reaction zone,
   (e) recovering an alkylate as product from zone S.

8. A process according to claim 7, in which a n-paraffin is recovered from zone S as a purge.

9. A process according to claim 7, in which the catalytic bed is washed in the reaction zone using said isoparaffin-rich fraction extracted from said zone S and designated (iii) in step (a).

10. A process according to claim 7 in which the recycle carried out at (a) of at least a portion of the reaction effluent (ii) is carried out at several levels in the reaction zone.

11. A process according to claim 7 in which the recycle carried out at (a) of a portion of the isoparaffin-rich fraction (ii) is carried out at different levels of the catalytic bed.

12. A process according to claim 7 in which in step (a), the elements (i), (ii) and optionally (iii) are mixed before being introduced into reaction zone R.

13. A process according to claim 1 in which, before introduction of the feed into the reaction zone, the feed is dried over a molecular sieve and selectively hydrogenated to eliminate at least the major portion of the highly unsaturated compounds it may contain.

14. A process according to claim 4, in which the ratio of the molar flow rates of the isoparaffin extracted from the separation or fractionation zone S and the alkylate extracted from the same zone is between 5:1 and 100:1.

15. A process according to claim 14, in which said ratio is between 10:1 and 50:1.

16. A process according to claim 1, in which a catalytic bed rejuvenation treatment is carried out at a frequency corresponding to a catalyst age (expressed as the weight of alkylate produced per weight of catalyst) of between 0.01 and 50 g/g.

17. A process according to claim 4, in which the duration of said process is between 1 minute and 10 hours.

18. A process according to any one of claim 1, in which the alkylation reaction is carried out in at least two reaction zones disposed in series and in which the isoparaffin to be treated is introduced into the first reaction zone crossed by the feed, in which the olefin is introduced into each reaction zone and in which the isoparaffin extracted from zone S is recycled to the first reaction zone.

19. A process according to claim 1, in which the alkylation reaction is carried out in at least two reaction zones disposed in parallel, each reaction zone being supplied with olefin to be treated, with isoparaffin to be treated and with recycled isoparaffin from zone S.

20. A process according to claim 1 in which, after several catalytic rejuvenation treatments, at least a portion of said catalytic bed is extracted, said portion of catalytic bed being replaced by regenerated or fresh catalyst.

* * * * *